United States Patent [19]

Islam et al.

[11] Patent Number: 5,990,160
[45] Date of Patent: Nov. 23, 1999

[54] USE OF TROPOLONE DERIVATIVES AS INHIBITORS OF THE ENZYME INOSITOL MONOPHOSPHATASE

[75] Inventors: Khalid Islam, Como; Stefania Stefanelli, Legnano; Federica Sponga, Saronno, all of Italy; Maurizio Denaro, San Diego, Calif.

[73] Assignee: Gruppo Lepetit, SpA, Milan, Italy

[21] Appl. No.: 09/312,733

[22] Filed: May 14, 1999

Related U.S. Application Data

[63] Continuation of application No. 08/945,120, Oct. 15, 1997, abandoned, which is a continuation of application No. PCT/EP96/02160, May 20, 1996.

[30] Foreign Application Priority Data

May 24, 1995 [GB] United Kingdom ................ 95107936

[51] Int. Cl.⁶ .................. A01N 37/00; A61K 31/185; C12Q 1/42

[52] U.S. Cl. .................. 514/470; 514/473; 514/553; 514/574; 435/7.4; 435/7.71; 435/7.72; 435/7.9; 435/7.91; 435/21

[58] Field of Search .................. 514/470, 473, 514/553, 574; 435/7.4, 7.71, 7.72, 7.9, 21, 7.91

[56] References Cited

U.S. PATENT DOCUMENTS

4,981,980  1/1991  Giocobbe et al. ................ 514/345

OTHER PUBLICATIONS

Chemical Abstract 77:111266, "Biosynthesis of the Fungal Tropolones Puberulonic and Puberulic Acids", Nov. 1972.

*Primary Examiner*—Frederick Krass
*Attorney, Agent, or Firm*—Ruth E. Homan

[57] ABSTRACT

The present invention concerns the use of puberulic or puberulonic acid as inhibitors of the enzyme iositol monophosphatase (EC 3.1.3.25) and thus useful in the treatment of manic or depressive symptoms.

2 Claims, No Drawings

USE OF TROPOLONE DERIVATIVES AS INHIBITORS OF THE ENZYME INOSITOL MONOPHOSPHATASE

This application is a continuation of U.S. Ser. No. 08/945,120, filed Oct. 15, 1997 and now abandoned, which is a continuation of PCT/EP96/02160, filed May 20, 1996.

This invention relates to the use of some tropolone derivatives as inhibitors of the enzyme inositol monophosphatase (EC 3.1.3.25), hereinafter referred to with the acronym "IMPase".

The present invention also relates to the use of these compounds in the treatment of mania and depression symptoms and pharmaceutical formulations comprising said compounds as active ingredient; the compounds of the invention may also be used in analytical methods for detecting IMPase.

More specifically, said tropolones derivatives are known compounds of formula I

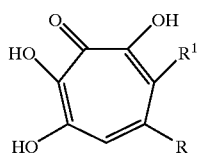

wherein R is a carboxylic group and $R^1$ is hydrogen or R and $R^1$ taken together with the adjacent carbon atoms form a heterocycle ring of formula:

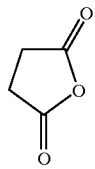

When R is a carboxylic group and $R^1$ is hydrogen in the above formula, the compound is puberulic acid (i.e. 3,4,6-trihydroxy-5-oxo-1,3,6-cycloheptatriene-1-carboxylic acid), while when R and $R^1$ taken together with the adjacent carbon atoms form a heterocycle ring as above defined, the compound is puberulonic acid (i.e. 3,4,6-trihydroxy-5-oxo-1,3,6-cycloheptatriene-1,7-dicarboxylic acid anhydride). As known in the art, the tautomeric forms of the compounds of formula I are equivalent one to each other and thus are encompassed by the present formula.

Although these compounds had already been isolated in the early 30's, as described by Birkinshaw et al., Biochem. Jour. 26, 441 (1932), their structure was determined only about fifteen years later, as disclosed by Corbett et al. Jour. Chem. Soc., 1950, 6. Some years later, also the chemical synthesis of said tropolones derivatives was disclosed by Johns et al., Jour. Chem. Soc. 1954, 198 and by Nozoe et al., Bull. Chem. Soc. Jap., 33, 1071 (1960).

Puberulic and puberulonic acid, as other tropolone derivatives, are known to have antimicrobial activity, while for some other tropolone derivatives an antineoplastic activity or an antiallergic activity has been described; see for instance Yamato M. et al., Jour. Med. Chem. 30(10), 1897–1900 (1987) or Bagli J. F., Jour. Med. Chem. 22(10), 1186 (1979), respectively.

In anti-manic and anti-depressive therapies, the use of lithium, preferably employed in the form of lithium carbonate, is known for alleviating manic symptoms, normalizing the mood of manic patients rather than compensating the excesses of the manic state through sedation or "tranquillization". Furthermore, it seems to be the only drug in psychiatry for which clear prophylaxis against disease recurrences and deterioration has been demonstrated. Lithium shows its clearest effects in bipolar disorders, which include both mania and depression, or only mania; these disorders are subdivided into Bipolar I and II disorders. In the former cases, there is presence of a full-blown manic episode, while in the latter case there is mild hypomania only.

Despite its therapeutic properties, a number of issues detract from the therapeutic utility of lithium. Antipsychotic drugs are the first pharmacologic mode of treatment of acute bipolar disorder, unless the patient is manageable enough to wait the 7–10 days it takes for lithium to exert its anti-manic effect. A costly prelithium workup is required because of the adverse effects common to lithium therapy. As a matter of fact, lithium can cause a transient leukocytosis, can cause patients with a borderline thyroid reserve to become clinically hypothyroid, and can decompensate cardiac status due to shifts in fluids and electrolytes.

It has been observed that the polyuria-polydipsia syndrome occurs in up to 60% of treated patients. Structural lesions in kidney, such as interstitial fibrosis, tubular atrophy and glomerular sclerosis, are reported after chronic lithium treatment, especially in patients who have experienced lithium toxicity. Other adverse effects of lithium include tremor, weight gain, diarrhea and skin rash. These side effects are serious practical deterrents to the use of lithium in clinical practice.

Side effects, especially the more serious ones, can be reduced by monitoring plasma lithium concentrations in bipolar patients. The need to monitor plasma drug concentrations, and to maintain these within a narrow therapeutic range, destract from its clinical utility.

An ideal lithium mimetic agent would have a rapid onset of action in both bipolar and non-bipolar depression, require only once-a-day dosing, and have a safety profile requiring no extensive pretreatment medical evaluation, no plasma drug monitoring, nor be associated with as severe a spectrum of side effects as lithium, per se.

It was demonstrated that inositol monophosphatase is a key enzyme in the phosphoinositide cycle and is responsible for the provision of inositol by dephosphorylation of inositol-1-phosphate, inositol-3-phosphate, and inositol-4-phosphate; as lithium inhibits the activity of said enzyme, it has been suggested that this inhibition is likely to be the molecular mechanism by which lithium exerts its anti-manic and anti-depressive activity.

In this view, development of potent and specific inhibitors of IMPase, could lead to completely novel drugs effective for the treatment of mania and depression.

Suitable compounds which show said inhibiting activity against IMPase are the compounds of formula I.

As mentioned above, the compounds of formula I may be obtained either by microbial or by chemical synthesis.

When microbial synthesis is followed, puberulonic acid is generally obtained in a larger amount with respect to puberulic acid and thus the latter is preferably obtained by means of a decarboxylating reaction of puberulonic acid.

The microbial process for obtaining puberulonic acid comprises:

a) Cultivating under aerobic conditions in an aqueous nutrient medium containing assimilable sources of carbon, nitrogen, and inorganic salts a fungus of the genus Penicillium capable of producing the IMPase-inhibiting compounds of the invention;

b) recovering the IMPase-inhibiting compounds from the fermentation broth and/or from the mycelium;

c) purifying and isolating puberulonic acid according to known per se techniques.

Suitable microorganisms of the Penicillium genus for the above process are *P. puberulum, P. aurantiovirens, P. johannioli* and *P. cyclopium viridicatum*, which may be fermented according to the known techniques, for instance as described in the above cited reference (i.e. Birkinshaw et al.) or by Oxford et al., Chem. Ind. 1942, 61, 485.

The medium used for cultivating the producing strain may be any fluid or solid medium containing the nutrients which the particular microorganisms are able to utilize, although a fluid medium is preferable for commercial scale operations.

As known in the art, the composition of the nutrient medium may be varied over a wide range, provided that carbon and nitrogen sources are present in the fermentation medium. Typical sources of carbon include: glucose, lactose, maltose, galactose, sucrose, dextrin, fats and oils (e.g. soybean oil, lard oil, chicken oil), starches, glycerol, mannitol, sorbitol and the like. Typical nitrogen sources include: ammonia, ammonium sulfate, amino acids such as glycine, arginine, threonine, methionine, tryptone, peptone, complex sources such as yeast autolysates, malts, soy, cotton seed, tomato paste, corn steep liquor, yeast extract, meat extract and fermentation by-products such as whole yeast and distillers solubles. Other essential nutrients are provided via the mineral salts such as the chlorides, nitrates, sulfates, carbonates and phosphates of sodium, potassium, ammonium, magnesium and calcium. The nutrient medium may also contain sources of inorganic trace elements such as magnesium, iron, copper, manganese, zinc, cobalt, cadmium, molybdenum and the like. It is, of course, possible to add inorganic or organic acids, alkalies, buffers, etc. for the purpose of adjusting the pH of the medium, or to add suitable amounts of oils, surfactants, etc. for defoaming purposes.

Ordinarily, the producing strain is pre-cultured in a shake flask, then the culture is used to inoculate jar fermentors for production of substantial quantities of the IMPase-inhibiting substances. The medium used for the pre-culture can be the same as that employed for larger fermentations, but other media can also be employed.

The producing strain is generally grown at temperatures of from 20° C. to 40° C., preferably 24° C. to 35° C., particularly preferred is a temperature of about 25° C.

The fermentation may be carried out by any procedure such as stationary, shake or aerobic stirred culture; preferably shaking or surface culture are employed, particularly preferred being the fermentation on a rotary shaker.

Agitation and aeration of the culture mixture may be accomplished in a variety of ways. Agitation may be provided by a propeller or similar mechanical agitation equipment, by revolving or by shaking the fermentor, by various pumping equipment or by passage of sterile air through the medium. Aeration may be effected by passing sterile air through the fermentation mixture.

During fermentation, the production of the IMPase-inhibiting compounds can be monitored by testing broth or mycelial extract samples for IMPase-inhibiting activity, for instance, by bioassays or TLC or HPLC procedures.

In general, fermentation is completed in about 3 to 5 days.

The recovery of the IMPase-inhibiting compounds from the mycelium or the fermentation broths of the producing microorganisms is conducted according to known per se techniques such as extraction with solvents, precipitation by adding non-solvents or by changing the pH of the solution, partition chromatography, reverse-phase partition chromatography, ion-exchange chromatography, molecular exclusion chromatography and the like.

A preferred procedure for recovering the crude IMPase-inhibiting substances of the invention involves extracting the filtered or centrifuged mycelium with a water-miscible organic solvent, concentrating the extracts and recovering the crude IMPase-inhibiting substances by precipitation, optionally with the addition of a precipitating agent, by extraction of the aqueous residue with a water immiscible organic solvent or by adsorption chromatography followed by elution of the desired product from the adsorption matrix; preferably, the crude IMPase-inhibiting substances are recovered by means of adsorption chromatography.

Examples of stationary phases which are usefully employed in the above chromatographic adsorption step, are allumina, diatomaceous earth, carbon, polystyrene resins (e.g. Amberlite XAD2 or XAD4, Rohm and Haas; Dowex M112 or S112, Dow Chemical Co.; Diaion HP 20, Mitsubishi), acrylic resins (e.g. XAD7 or XAD8, Rohm and Haas), polyamide resins such as polycaprolactames, nylons and cross-linked polyvinylpyrrolidones (e.g. Polyamide-CC 6, Polyamide-SC 6, Polyamide-CC 6.6, Polyamide-CC 6AC and Polyamide-SC 6AC, Macherey-Nagel & Co., West Germany; PA 400, M. Woelm AG, West Germany and the polyvinylpyrrolidone resin PVP-CL, Aldrich Chemie GmbH & Co., KG, West Germany) and controlled pore cross-linked dextrans (e.g. Sephadex LH-20, Pharmacia Fine Chemicals, Ab). Preferably, polystyrene resins are employed, particularly preferred being the S112 resin.

The preferred solvent for eluting the IMPase-inhibiting compounds from the adsorption matrix depends on the specific stationary phase.

For instance, when silica gel or alumina is employed, preferred solvents are halogenated hydrocarbons, lower alkanols, ethers, higher ketones and mixtures thereof; lower ketone such as acetone or a lower alcohol such as methanol may be used with carbon as stationary phase; water-miscible solvents or mixture thereof, such as ethanol, are preferred eluents for polystyrene or acrylic resins, while aqueous mixture of water-miscible solvents are preferred for polyamide resins.

Purification of the crude puberulonic acid is obtained according to known per se techniques, for instance by suspending the crude product in a suitable organic solvent, such as methanol, and removing the precipitate. Puberulonic acid is then separated by means of known chromatographic techniques; for instance, a separation system may be used, which comprises controlled pore cross-linked dextrans as stationary phase (e.g. Sephadex LH-20, Pharmacia Fine Chemicals, Ab) and methanol as mobile phase. The powder obtained by collecting and concentrating under vacuum the active fractions may be further purified by ion-exchange chromatography. For instance it may be redissolved in a buffered solution (e.g. 0.02M sodium acetate, pH 5.5) and the obtained solution is applied on the top of a chromatographic column containing cross-linked agarose resin (e.g. Q-Sepharose, Pharmacia) which is eluted with an aqueous solution of 1N hydrochloric acid, preferably with a gradient from 10% to 20%.

Puberulic acid is then obtained by decarboxylation of puberulonic acid, as described by Corbett et al. Jour. Chem. Soc., 1950, 6.

Puberulic acid is also obtainable by direct chemical synthesis, as disclosed by Johns et al., Jour. Chem. Soc.

1954, 198. According to this method, a solution of 3,4,6-trimethoxycycloheptatriene-caboxylic acid (an intermediate obtained by reacting diazoacetic ester and 1,2,4-trimethoxybenzene) in chloroform is reacted with a solution of bromine in carbon tetrachloride; the obtained precipitate is then heated in ethyl acetate, cooled in ice and then hydrolyzed with hydrobromic acid, obtaining stipitatic acid. Said stipitatic acid is then reacted with bromine, in order to obtain monobromostipitatic acid which is in turn reacted with potassium hydroxide to obtain the desired puberulic acid.

The chemical synthesis of puberulonic acid described by Nozoe et al., Bull. Chem. Soc. Jap., 33, 1071 (1960), involves the reaction of tropolone-3,4-dicarboxylic anhydride (obtained by alkaline hydrogen peroxide oxidation of purpurogallin) with bromine in acetic acid, thus obtaining the 7-bromotropolone-3,4-dicarboxylic anhydride which is in turn reacted with a mixture of sodium β-naphtalensulfonate, sodium hydroxide and copper powder, yielding 3-hydroxy-tropolone-4,5-dicarboxylic anhydride. By repeating the above two steps, a further hydroxy group is inserted in the molecule, thus obtaining the desired puberulonic acid.

For determining the activity of the compounds of formula I, IMPase with a purity higher than 90% as judged by SDS-PAGE (sodium dodecyl sulphate polyacrylamide gel electrophoresis) is purified as described in P. D. Pelton and A. J. Ganzhorn, Journal Biolog. Chem., 267, 1992, pp. 5916–5920. The enzyme can be purified from animal brain or from recombinant *E. coli* strains expressing animal IMPase. Although crude enzyme preparations can also be used, it is preferable to use purified enzyme. The purified enzyme routinely has a specific activity of 25 μmol of Pi/min/mg of protein as determined in a standard assay (P. V. Attwood et al., Biochem. Jour., 1988, 253, pp. 387–394) with 4 mM 2-glycerolphosphate as substrate.

The enzyme activity may be determined according to A. J. Ganzhorn and M. C. Chanal, Biochem., 1990, 29; the reaction mixture contains 50 mM Tris-HCl, pH 7.5, 2 mM magnesium chloride and 0.1 mM EGTA. Then, 5 μg/ml of enzyme IMPase and 4 mM of 2-glycerolphosphate substrate are added to the reaction mixture; alternatively, it is also possible to add the substrate directly into the reaction mixture, before adding the enzyme.

The reaction is considered terminated after 30 minutes from the addition of the substrate or the enzyme (depending on which one is added later); the liberated phosphate is determined by molybdate coloration (P. V. Attwood et al., Biochem. Jour., 1988, 253, pp. 387–394) at 350 nm with a Shimadzu spectrophotometer UV 2100.

The enzyme reaction is performed either in the absence or in the presence of various concentrations of the compounds of formula I, to determine the molar amount of inhibitor required to inhibit the enzyme activity by 50% (IC50).

Said IC50 value is about 4 μM for puberulonic acid and about 40 μM for puberulic acid, much lower than the one of lithium, which is about 1250 μM.

On the basis of the above results the compounds of formula I may find application in the therapeutic field as anti-manic and anti-depressive agent.

For the treatment of manic or depressive symphtoms, the compounds of the invention can be administered as such or formulated with pharmaceutically acceptable carriers; the administration may be done orally, parenterally or rectally.

For oral administration, the compounds of the invention can be formulated into solid or liquid preparations such as capsules, pills, tablets, troches, powder, syrups, solutions, suspensions or emulsions.

For preparing solid compositions such as tablets, the principal active ingredient is mixed with a pharmaceutical carrier, i.e. conventional tableting ingredients such as lactose, sucrose and cornstarch in combination with binders, such as acacia, cornstarch or gelatin, disintegrating agents such as potato starch or alginic acid, lubricants such as stearic acid or magnesium stearate and other pharmaceutical diluents, e.g. water, to form a solid preformulation composition containing a homogeneous mixture. When referring to these preformulation compositions as homogeneous, it is meant that the active ingredient is dispersed evenly throughout the composition, so that the composition may be readily subdivided into equally effective unit dosage forms such as tablets, pills, capsules, and the like. This solid preformulation composition is then subdivided into unit dosage forms of the type described above containing from 50 to about 350 mg of the active ingredient of the present invention. The tablets or pills of the novel compositions can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in the release.

The liquid forms in which the novel composition of the present invention may be incorporated for oral administration include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone, gelatin and the like.

For parenteral administration, the compounds of the invention may be formulated into suitable injectable preparations containing a liquid vehicle. Such vehicle normally has no therapeutic effect and should not be toxic. Examples of suitable vehicles for preparing injectable dosage forms of the compounds of the invention are water, aqueous vehicles (e.g. Sodium chloride injections, Dextrose injections, etc.), water miscible solvents (e.g. ethyl alcohol, polyethylene glycol, propylene glycol, etc.) and non-aqueous vehicles (e.g. "fixed oils" such as corn oil, cottonseed oil, peanut oil and sesame oil). Optionally, the injectable preparation may further contain buffers for stabilizing the solution (e.g. citrates, acetates and phosphates) and/or antioxidants (e.g. ascorbic acid or sodium bisulfite). The desired route of parenteral administration will place requirements on the specific formulation. For example, suspensions would not be administered directly in the blood stream because of the danger of insoluble particles blocking capillaries, whilst solutions to be administered subcutaneously would require strict attention to tonicity adjustment, otherwise irritation of the nerve endings in the anatomical area would give rise to pronounced pain.

Useful indications for the preparations of suitable oral, parenteral or rectal dosage forms can be found in: Remington's Pharmaceutical Sciences, 17th Edition, 1985, 1985 (Merck Publishing Company, Easton, Pa.).

The dosage of the active ingredient depends on many factors which include type, age and conditions of the patient, specific active ingredient and formulation selected for the administration, administration schedule, etc.

In general, a dosage level of about 1–20 mg/kg/day, on a regimen of 1–4 times a day, is preferred.

It is understood that the exact treatment level will depend upon the case history of the patient being treated and in the last analysis the precise treatment level falling within the above guidelines is left to the discretion of the therapist.

The following are illustrative examples for preparing the compounds of the invention.

EXAMPLE 1

Fermentation of *Penicillum puberulum*

*Penicillium puberulum* ATCC 8732 is fermented in Czapek-Dox medium, as described by Birkinshaw et al., Biochem. Jour. 26, 441 (1932).

EXAMPLE 2

Recovery of Puberulonic Acid

The fermentation broth obtained according to Example 1 is harvested and the mycelium is removed by filtration with Hyflo® filter matrix. Puberulonic acid is adsorbed from the filtrate broth (at pH 3.5, for 3 hours stirring, batch-wise) onto 450 ml of S112® polystyrene resin (The Dow Chemical Company). The resin is then recovered, washed with water and eluted with 1.5 l of a mixture of acetone:BuOH:water, 8:1:1. The eluates are concentrated under reduced pressure and the aqueous residue lyophilized to yield 12.2 g of crude puberulonic acid. Crude puberulonic acid can also be obtained by precipitation with a non-polar solvent such as diethyl ether, then filtering and desiccating the precipitate.

EXAMPLE 3

Purification of Puberulonic Acid 5 g of crude preparation (obtained according to Example 2) is suspended in methanol, the precipitate is separated by centrifuge and discarded. The supernatant is concentrated under reduced pressure and the obtained sample is then applied to the top of a Sephadex® LH-20 column (bead diameter 25–100 µm, Pharmacia; column: 6×50 cm) previously equilibrated in methanol.

A stepwise fractionation of the crude antibiotic is carried out, without pressure, by elution with methanol. The active fractions (tested with enzymatic assay) are collected and concentrated under vacuum. The solid is then redissolved in water and lyophilized obtaining 60 mg of powder.

40 mg of the above powder are dissolved in 30 ml of sodium acetate (0.02 M, pH 5.5) and then applied to the top of a Q-Sepharose® column (bead diameter 24–44 µm, Pharmacia; column: 1.5×12 cm) previously equilibrated with the same buffer. After the complete adsorption of the material, the column is washed with 200 ml of deionized water. The elution is carried out by elution with water/1N HCl, step gradient from 10% to 20% of HCl. The active fractions are collected, extracted with ethyl acetate at acidic pH, concentrated under reduced pressure and lyophilized from water yielding 10 mg of yellow powder.

EXAMPLE 4

Decarboxylation of Puberulonic Acid 5 mg of puberulonic acid are dissolved in 300 µl of water and treated at 105° for 15 hours under nitrogen, using a Pico-tag apparatus (Waters-Millipore). The reaction solution is freeze dried, obtaining about 3 mg of puberulic acid.

We claim:

1. A method for in vitro testing, wherein puberulic or puberulonic acid inhibits the enzyme inositol monophosphatase EC 3.1.3.25.

2. A method for treating manic or depressive symptoms by inhibiting the enzyme inositol Monophosphatase EC 3.1.3.25, which comprises administering an effective amount of puberulic or puberulonic acid to a patient in need thereof.

* * * * *